US008288107B2

(12) United States Patent
Teem

(10) Patent No.: US 8,288,107 B2
(45) Date of Patent: Oct. 16, 2012

(54) MATERIALS AND METHODS FOR DETECTING INTERACTION OF CFTR POLYPEPTIDES

(75) Inventor: John L. Teem, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 961 days.

(21) Appl. No.: 11/821,812

(22) Filed: Jun. 25, 2007

(65) Prior Publication Data

US 2008/0167259 A1    Jul. 10, 2008

Related U.S. Application Data

(63) Continuation of application No. 10/089,875, filed as application No. PCT/US00/27900 on Oct. 6, 2000, now Pat. No. 7,238,474.

(60) Provisional application No. 60/157,996, filed on Oct. 6, 1999, provisional application No. 60/181,892, filed on Feb. 11, 2000, provisional application No. 60/182,373, filed on Feb. 14, 2000.

(51) Int. Cl.
*C12Q 1/68* (2006.01)
*C12N 1/19* (2006.01)
*C12N 15/85* (2006.01)

(52) U.S. Cl. ............... 435/6.13; 435/6.1; 435/254.2; 435/325

(58) Field of Classification Search .................. None
See application file for complete search history.

(56) References Cited

U.S. PATENT DOCUMENTS

| | | | |
|---|---|---|---|
| 5,283,173 | A | 2/1994 | Fields et al. |
| 5,468,614 | A | 11/1995 | Fields et al. |
| 5,543,399 | A | 8/1996 | Riordan et al. |
| 5,667,973 | A | 9/1997 | Fields et al. |
| 5,674,898 | A | 10/1997 | Cheng et al. |
| 5,750,571 | A | 5/1998 | Cheng et al. |
| 5,876,974 | A | 3/1999 | Gregory |
| 5,900,360 | A | 5/1999 | Welch et al. |
| 5,939,536 | A | 8/1999 | O'Riordan et al. |
| 5,981,714 | A | 11/1999 | Cheng et al. |
| 6,093,567 | A | 7/2000 | Gregory et al. |
| 6,270,954 | B1 | 8/2001 | Welch et al. |
| 6,316,223 | B1 | 11/2001 | Payan et al. |

FOREIGN PATENT DOCUMENTS

| | | |
|---|---|---|
| CA | 2037478 | 9/1991 |
| EP | 0 446 017 A1 | 9/1991 |
| WO | WO 94/04671 A1 | 3/1994 |
| WO | WO 94/25607 A1 | 11/1994 |
| WO | WO 97/37645 A1 | 10/1997 |

OTHER PUBLICATIONS

Biodiversity, Ch. 9: Screening Plants for New Medicines, National Academy Press, 1988, pp. 83-97.*
Niderman et al. Pathogenesis-related PR-1 proteins are antifungal. Isolation and characterization of three 14-kilodalton proteins of tomato and of a basic PR-1 of tobacco with inhibitory activity against Phytophthora infestans. Plant Physiol. May 1995;108(1):17-27.*
Talaro et al, Microbiology, Wm. C. Brown Publishers, 1993, p. 317.*
Annereau, J. P. et al. "Insight into Cystic Fibrosis by Structural Modelling of CFTR First Nucleotide Binding Fold (NBF1)" *C. R. Acad. Sci. Paris, Sciences de la vie/Life Sciences*, 1997, pp. 113-121, vol. 320.
Aronheim, A. et al. "Isolation of an AP-1 Repressor by a Novel Method for Detecting Protein Interactions" *Molecular and Cellular Biology*, 1997, pp. 3094-3102, vol. 17. No. 6.
Berlin, V. "Protein Interactions Mediated by Small Molecule Ligands" *Variations on the Two-Hybrid Theme*, 1997, pp. 259-272, Oxford University Press, New York.
Brown, C. R. et aL "Chemical Chaperones Correct the Mutant Phenotype of the ΔF508 Cystic Fibrosis Transmembrane Conductance Regulator Protein" *Cell Stress & Chaperones*, 1996, pp. 117-125, vol. 1, No. 2.
Cheng, S. H. et al. "Defective Intracellular Transport and Processing of CFTR Is the Molecular Basis of Most Cystic Fibrosis" *Cell*, 1990, pp. 827-834, vol. 63.
Denning, G. M. et al. "Processing of Mutant Cystic Fibrosis Transmembrane Conductance Regulator is Temperature-Sensitive" *Nature*, 1992, pp. 761-764, vol. 358, No. 6389.
Flotte, T. R. et al. "Adeno-associated Virus Vector Gene Expression Occurs in Nondividing Cells in the Absence of Vector DNA Integration" *American Journal of Respiratory Cell and Molecular Biology*, 1994, pp. 517-521, vol. 11.
Gregory, R. J. et aL "Maturation and Function of Cystic Fibrosis Transmembrane Conductance Regulator Variants Bearing Mutations in Putative Nucleotide-Binding Domains 1 and 2" *Molecular and Cellular Biology*, 1991, pp. 3886-3893, vol. 11, No. 8.
Hallows, K. R. et al. "Inhibition of Cystic Fibrosis Transmembrane Conductance Regulator by Novel Interaction with the Metabolic Sensor AMP-Activated Protein Kinase" *The Journal of Clinical Investigation*, 2000, pp. 1711-1721, vol. 105. No. 12.
Johnsson, N. et aL "Split Ubiquitin—A Sensor of Protein Interactions in Vivo" *The Yeast Two-Hybrid System*, 1997, pp. 316-332, Oxford University Press, New York.
Karimova, G. et al. "A Bacterial Two-Hybrid System Based on a Reconstituted Signal Transduction Pathway" *Proc. Natl. Acad. Sci.*, 1998, pp. 5752-5756, vol. 95.
Keegan, L. et al. "Separation of DNA Binding from the Transcription-Activating Function of a Eukaryotic Regulatory Protein" *Science*, 1986, pp. 699-704, vol. 231.

(Continued)

*Primary Examiner* — Michele K Joike
(74) *Attorney, Agent, or Firm* — Saliwanchik, Lloyd & Eisenschenk

(57) ABSTRACT

The subject invention concerns materials and methods for detecting the interaction of CFTR proteins. In one embodiment, the method can be used to determine whether one CFTR polypeptide interacts with a second CFTR polypeptide. The subject invention also concerns materials and methods for screening for drugs or compositions that can restore or enhance interaction of CFTR proteins containing mutation(s) that reduce or prevent dimerization of the proteins. The assay of the present invention can be used to screen a large number of compounds in a high throughput format. The subject invention also pertains to host cells useful in the methods of the invention. The subject invention also concerns compositions and methods for treating patients afflicted with cystic fibrosis.

19 Claims, 2 Drawing Sheets

OTHER PUBLICATIONS

Kerem, B-S. et al. "Identification of the Cystic Fibrosis Gene: Genetic Analysis" *Science*, 1989, pp. 1073-1080 vol. 245.

Kunzelman, K. et al. "Inhibition of Epithelial Na+ Currents by Intracellular Domains of the Cystic Fibrosis Transmembrane Conductance Regulator" *FEBS Letters*, 1997, pp. 341-344, vol. 18020.

Ma, J. et al. "Deletion Analysis of GAL4 Defines Two Transcriptional Activating Segments" *Cell*, 1987, pp. 847-853, vol. 48.

Neville, D. C. A. et al. "Expression and Characterization of the NBD1-R Domain Region of CFTR: Evidence for Subunit—Subunit Interactions" *Biochemistry*, 1998, pp. 2401-2409, vol. 37.

Riordan, J. R. et al. "Identification of the Cystic Fibrosis Gene: Cloning and Characterization of Complementary DNA" *Science*, 1989, pp. 1066-1072, vol. 245.

Rommens, J. M. et al. "Identification of the Cystic Fibrosis Gene: Chromosome Walking and Jumping" *Science*, 1989, pp. 1059-1065, vol. 245.

Sato, S. et al. "Glycerol Reverses the Misfolding Phenotype of the Most Common Cystic Fibrosis Mutation" *The Journal of Biological Chemistry*, 1996, pp. 635-638, vol. 271, No. 2.

Sheppard, D. N. et al. "Expression of Cystic Fibrosis Transmembrane Conductance Regulator in a Model Epithelium" *American Physiological Society*, 1994, pp. L405-L413, vol. 266.

Sheppard, D. N. et al. "Mutations in CFTR Associated with Mild-Disease-Form CI Channels with Altered Pore Properties" *Nature*, 1993, pp. 160-164, vol. 362.

Swick, Andrew G. et al., "Promoter—cDNA-Directed Heterologous Protein Expression in *Xenopus laevis oocytes*" *Proc. Natl. Acad. Sci.*, 1992, pp. 1812-1816, vol. 89.

Teem, J. L. et al. "Identification of Revertants for the Cystic Fibrosis ΔF508 Mutation Using STE6-CFTR Chimeras in Yeast" *Cell*, 1993, pp. 335-346, vol. 73.

Teem, J. L. et al. "Mutation of R555 in CFTR-ΔF508 Enhances Function and Partially Corrects Defective Processing" *Receptors and Channels*, 1996, pp. 63-72, vol. 4.

Thoreau, V. et al. "Molecular Cloning, Expression Analysis, and Chromosomal Localization of Human Syntaxin 8 (STX8)" *Biochemical and Biophysical Research Communications*, 1999, pp. 577-583, vol. 257, No. 2.

Welsh, M. J. et al. "Cystic Fibrosis Gene Therapy Using an Adenovirus Vector: In Vivo Safety and Efficacy in Nasal Epithelium" *Human Gene Therapy*, 1994, pp. 209-219, vol. 5.

Welsh, M. J. et al. "Cystic Fibrosis: The Genetic Defects Underlying This Lethal Disease Have Now Been Shown to Eliminate or Hobble a Critical Channel through which a Constituent of Salt Enters and Leaves Cells" *Scientific American*, 1995, pp. 52-59.

Zabner, J. et al. "Adenovirus-Mediated Gene Transfer Transiently Corrects the Chloride Transport Defect in Nasal Epithelia of Patients with Cystic Fibrosis" *Cell*, 1993, pp. 207-216, vol. 75.

Zabner, J. et al. "Comparison of DNA-Lipid Complexes and DNA Alone for Gene Transfer to Cystic Fibrosis Airway Epithelia in Vivo" *Journal of Clinical Investigation*, 1997, pp. 1529-1537, vol. 100, No. 6.

Zerhusen, B. et al. "A single conductance pore for chloride ions formed by two cystic fibrosis transmembrane conductance regulator molecules" *J. Biol. Chem.*, Mar. 1999, pp. 7627-7630, vol. 274.

Brown, R. et al. "Correcting Temperature-sensitive Protein Folding Defects" *J. Clin. Invest.*, 1997, pp. 1432-1444, vol. 99.

Eskandari, S. et al. "Structural analysis of cloned plasma membrane proteins by freeze-fracture electron microscopy" *PNAS*, 1998, pp. 11235-11240, vol. 95.

Serebriiskii, I. et al. "A Two-hybrid Dual Bail System to Discriminate Specificity of Protein Interactions" *J. Biol. Chem.*, 1999, pp. 17080-17087, vol. 274.

* cited by examiner

MATERIALS AND METHODS FOR DETECTING INTERACTION OF CFTR POLYPEPTIDES

CROSS-REFERENCE TO RELATED APPLICATIONS

This application is a continuation of U.S. application Ser. No. 10/089,875, filed Apr. 3, 2002, now U.S. Pat. No. 7,238, 474 which is the national stage of international application No. PCT/US00/27900, filed Oct. 6, 2000, which claims the benefit of U.S. Provisional Application No. 60/157,996, filed Oct. 6, 1999; U.S. Provisional Application No. 60/181,892, filed Feb. 11, 2000; and U.S. Provisional Application No. 60/182,373, filed Feb. 14, 2000, the disclosure of each of which is hereby incorporated by reference in their entirety, including all figures, nucleic acid sequences, amino acid sequences, and tables.

BACKGROUND OF THE INVENTION

Cystic fibrosis (CF) is the most common genetic disease of Caucasians in North America, occurring at a frequency of approximately 1 in 2500 births (Welsh et al., 1995). The disease results from defective function of the gene encoding the Cystic Fibrosis Transmembrane Conductance Regulator (CFTR) protein in a variety of tissues, including the pancreas and the lung epithelium. Riordan et al. (1989), Rommens et al. (1989) and Kerem et al. (1989) describe the cloning and sequencing of the CFTR gene. U.S. Pat. No. 5,543,399 to Riordan et al. discloses the purification of CFTR protein.

Normal CFTR protein is a membrane protein that functions as a cAMP-regulated chloride channel. The ΔF508 mutation in the CFTR gene, which is characterized by a deletion of the phenylalanine amino acid at position 508 of the CFTR protein, is the defect associated with most cases of CF. A CFTR protein having the ΔF508 mutation does not exit the ER and proceed on to the plasma membrane (Cheng et al., 1990; Gregory et al., 1991). It has been found that the ΔF508 mutation causes the temperature-sensitive misprocessing of the mutant protein that prevents the protein from exiting the ER (Denning et al., 1992).

The absence of CFTR protein in the pancreatic duct results in the blockage of the duct by a thick mucus that prevents pancreatic enzymes from passing from the pancreas to the intestine. Without treatment, CF patients decline as a consequence of malnutrition associated with insufficient pancreatic function. However, pancreatic enzymes may be introduced into the diet of CF patients as a means of reversing the effects of pancreatic insufficiency.

Unlike in the pancreas, the absence of CFTR function in lung epithelium results in a severe lung disease that cannot be readily reversed or controlled by conventional treatment. Lack of CFTR function in the lung results in airway fluid with an altered ion composition, thereby creating a favorable environment for disease-causing bacteria to colonize the lung. Additionally, mucus secreted into the lung becomes thick and viscous, preventing normal clearing of the bacteria from the airways. The chronic bacterial infection leads to destruction of lung tissue and loss of lung function. Current treatments for CF lung disease involve physical therapy to aid mucus clearance and antibiotic therapy to treat the lung infection. Although these treatments slow the progression of disease, they do not reverse it. Patients with CF consequently die prematurely, usually by the age of 30.

CF cells lack CFTR chloride channel activity because they have mutant CFTR genes that encode a defective CFTR protein. Thus, providing a patient with a copy of a normal human CFTR gene by way of gene therapy methods may provide an alternative to conventional therapies for the treatment of CF. Gene therapy strategies for the treatment of CF thus involve delivery of a normal wildtype human CFTR gene to mutant CF epithelial cells within the lung to restore normal CFTR chloride channel activity. Gene transfer of the CFTR gene can be accomplished by several different delivery methods. Recombinant viral vectors containing the wildtype CFTR gene provide one potential means to deliver the CFTR gene to CF cells. For example, recombinant adenovirus containing the wildtype CFTR gene have been shown to efficiently transfer the wildtype CFTR gene into CF epithelium, and correct the chloride channel defect (Welsh et al., 1994; Zabner et al., 1993). However, high doses of virus are generally required to obtain an efficacious response, which in time can cause inflammation resulting from the immune response to the viral proteins. Other viruses that might be used for CF gene therapy include AAV (Adeno-associated virus) (Flotte et al., 1994), retrovirus and lentivirus. The use of these viruses for gene therapy is also limited by the immune response to the high titer doses required for an efficacious response.

Gene transfer can also be achieved by transfection of CF cells by lipid-DNA complexes composed of plasmid DNA containing the CFTR cDNA in association with cationic or neutral lipids (Zabner et al., 1997). Gene therapy utilizing lipid-DNA complexes is a potential alternative to the use of viral vectors and presents a lower risk for an associated inflammatory immune response. However, gene transfer with lipid-DNA complexes is inefficient, so that only a small fraction of cells receive the therapeutic gene. As a consequence, only a very limited correction of the chloride channel defect is possible.

Another alternative for CF therapy is to identify drugs that have efficacy in treating the disease. However, the process of identifying potential drugs typically involves the screening of large numbers of compounds from a chemical library. Thus, the assay used to screen the library for active compounds must be specific for a desired activity, as well as rapid and cost effective. However, current drug screening strategies using mammalian cells and assays for CFTR chloride conductance are costly and labor intensive. Thus, there remains a need in the art for a means for rapidly screening potential drugs for the treatment of CF from among the hundreds of thousands of chemicals that can be tested.

BRIEF SUMMARY OF THE INVENTION

The subject invention concerns materials and methods for detecting the interaction of CFTR proteins. In one embodiment, the method can be used to determine whether one CFTR NBD1 polypeptide interacts with a second CFTR NBD1 polypeptide using a yeast dual hybrid assay. The subject methods can be used to determine whether mutations to the CFTR polypeptide reduce or eliminate dimerization of the CFTR polypeptides. The present methods can also be used to screen and identify revertant mutations that restore dimerization of a mutant CFTR polypeptide, as well as mutations that enhance dimerization and CFTR activity greater than that of wildtype protein.

The subject invention also provides materials and methods for efficiently identifying and screening for compounds, drugs and other such compositions that facilitate proper dimerization of the CFTR polypeptides. Compounds identified using materials and methods of the present invention are candidate agents for use in treating patients having CF. In one embodiment, a yeast dual hybrid assay is used to identify compounds that can restore dimerization of a protein comprising a region of a CFTR polypeptide having a mutation, such as ΔF508, that prevents dimerization. The assay methods of the present invention can be used to evaluate a large number of compounds in a high throughput format. The use of a yeast growth bioassay exemplified herein is fast and inexpensive in comparison to current screening procedures that involve mammalian cells and assays for CFTR channel activity.

The subject invention also concerns compositions and methods for treating CF. The compositions of the invention can be used to restore, promote or enhance the dimerization of CFTR protein and/or its exit from the ER and proper localization in the cell.

BRIEF DESCRIPTION OF THE DRAWINGS

(FIG. 2A) or 37° C. (FIG. 2B) (for 3 days and 5 days respectively). Glycerol was added to the media to a final concentration of 1.5 M as indicated (1.5 M Glyc) (FIG. 2C).

BRIEF DESCRIPTION OF THE SEQUENCES

Figure 1:
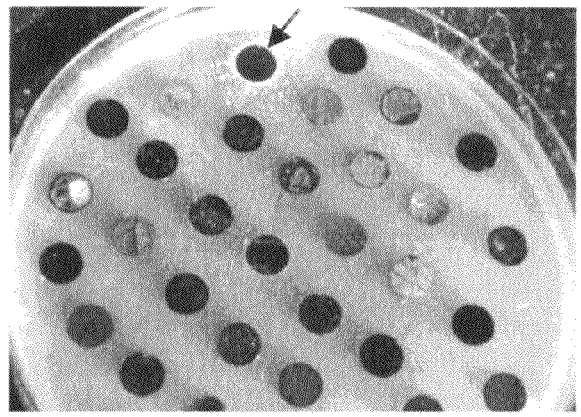
FIG. 1 shows an example of a plate with a positive-testing plant leaf disc on selective media using a yeast two-hybrid assay of the present invention.

SEQ ID NO:1 is a primer for PCR amplification of a fragment of a cDNA encoding CFTR.

SEQ ID NO:2 is a primer for PCR amplification of a fragment of a cDNA encoding CFTR.

SEQ ID NO:3 is a polynucleotide sequence that encodes a wildtype CFTR protein.

SEQ ID NO:4 is an amino acid sequence of a wildtype CFTR protein.

DETAILED DISCLOSURE OF THE INVENTION

The subject invention concerns materials and methods for detecting the interaction of cystic fibrosis transmembrane conductance regulator (CFTR) proteins. The method can be used to determine whether one CFTR polypeptide interacts with a second CFTR polypeptide. Preferably, the CFTR polypeptides are mammalian. More preferably, the CFTR polypeptides are human CFTR polypeptides. The methods of the present invention are based on the discovery that the wildtype CFTR protein forms dimers, and that dimerization is essential for the exit of the CFTR protein from the endoplasmic reticulum (ER). As described herein, a method of the present invention for detecting or determining the interaction of a first CFTR polypeptide with a second CFTR polypeptide comprises contacting the CFTR polypeptides and determining whether the polypeptides interact using a system where if interaction does occur then a detectable signal or change is induced in the assay system. In one embodiment, dimerization involves an association of the first nucleotide binding fold (NBD1) of one CFTR monomer with the NBD1 of another CFTR monomer. The methods of the present invention can model the temperature-sensitive misprocessing of mutant CFTR proteins.

In one embodiment, a method of the invention for detecting or determining the interaction of a first CFTR polypeptide with a second CFTR polypeptide comprises (a) providing a first fusion protein comprising all or a portion of a first CFTR protein and a DNA binding domain of a transcriptional activator that can bind to a site on a detectable reporter gene; (b) providing a second fusion protein comprising all or a portion of a second CFTR polypeptide and a transcriptional activation domain of a transcriptional activator that can activate transcription of the detectable reporter gene; (c) contacting the first fusion protein and the second fusion protein under conditions where if the first fusion protein and the second fusion protein interact then the interaction causes the transcriptional activation domain to activate transcription of the detectable reporter gene; and (d) detecting transcription of the detectable reporter gene or expression of the detectable reporter gene product. By "detectable gene" it is meant that expression of the gene or its gene product can be detected. The detectable gene can be engineered with sequences that bring the gene under control of the transcriptional activator. For example, where the GAL4 transcriptional activator is to be used, the UASG (upstream activation site, galactose) site (Keegan et al., 1986; Ma and Ptashne, 1987) can be incorporated upstream of the transcription start site of the detectable gene.

In a preferred embodiment, the fusion proteins are provided in a double transformant host cell, such as a yeast cell. The polynucleotide sequences encoding the fusion proteins can be incorporated into suitable expression vectors or plasmids, such as pAD-GAL4 or pBD-GAL4 for use in yeast cells. Other suitable vectors and plasmids are known in the art and can be readily selected by the ordinarily skilled artisan. Once the sequences encoding the fusion proteins are inserted in the vector or plasmid, the vector or plasmid can be incorporated into the host cell using standard methods, resulting in a double transformant host cell.

In additional embodiments, the interaction of a first CFTR polypeptide with a second CFTR polypeptide can be detected in a host cell by the interaction of signal transduction fusion proteins, or by the interaction of proteins resulting in cleavage of a ubiquitin fusion protein. These methods of detecting protein:protein interactions, by SOS recruitment (Aronheim et al., 1997) or by a split ubiquitin sensor (Johnsson and Varshavsky, 1997), respectively, are well known to those skilled in the art and are contemplated within the scope of methods of the present invention. The preferred host cell for these embodiments is yeast. In another embodiment, the interaction of a first CFTR polypeptide with a second CFTR polypeptide is detected by interaction of signal transduction fusion proteins within a bacterial cell. Methods for detecting protein:protein interactions in bacteria are also known by those skilled in the art (Karimova et al., 1998).

The CFTR portion of the fusion protein can contain one or more mutations of the wildtype amino acid sequence. The mutations contemplated can include amino acid substitutions, deletions and insertions. Any mutation, including mutations to CFTR already known in the art and associated with CF, can be prepared in the sequence of the CFTR polypeptide and used in the methods of the present invention. The CFTR protein of the fusion protein can include the entire coding sequence of the protein or a fragment thereof.

In one embodiment, dual hybrid systems can be used in the methods of the present invention. Dual hybrid systems are described in U.S. Pat. Nos. 5,283,173 and 5,468,614, which are herein incorporated by reference. Dual hybrid reagents are also available from commercial suppliers such as CLONTECH Laboratories (Palo Alto, Calif.) and Stratagene (La Jolla, Calif.). In a preferred embodiment, all or a portion of a first human or mammalian CFTR gene is cloned into a suitable plasmid that, when expressed in a host cell, provides a hybrid protein comprising a first CFTR protein, or a variant or fragment thereof, and a DNA-binding domain of a transcriptional activator that can bind to a site on a detectable gene in the host cell. All or a portion of a second human or mammalian CFTR gene is also cloned into a suitable plasmid that, when expressed in the host cell, provides a hybrid protein comprising a second CFTR protein, or a variant or fragment thereof, and a transcriptional activation domain that can activate transcription of the detectable gene in the host cell when the transcriptional activation domain is brought into close proximity with the detectable gene. Preferably, the first and second CFTR polypeptides are identical; however, the use of first and second CFTR polypeptides that are different, for example in amino acid sequence or length, is also contemplated within the scope of the present invention. The expression plasmids encoding the hybrid proteins can be introduced into a host cell using standard methods known in the art, such as electroporation or transfection by calcium phosphate precipitation. Preferably, the portion of the CFTR protein expressed in the hybrid proteins includes the first nucleotide binding domain (NBD1), or a functional fragment thereof, of human CFTR. The polynucleotides encoding the first and second fusion proteins are exposed to conditions where the fusion proteins are expressed. If the CFTR polypeptides of the expressed hybrid proteins interact, then the DNA binding domain and transcriptional activation domain of the transcriptional activator are brought into close proximity sufficient to cause transcription of the detectable gene. Where transcription or expression of the detectable gene is observed, this is indicative of interaction of the CFTR portion of the fusion proteins.

As taught herein, wildtype human CFTR used in the subject dual hybrid methods interact and result in transcription of the detectable gene in the host cell in the dual hybrid embodiment described herein. Mutations that reduce or prevent dimerization of CFTR proteins can be identified using the methods and materials of the present invention because these mutant CFTR proteins do not interact and, therefore, transcription of the detectable gene in the host cell does not occur. In an exemplified embodiment, the ΔF508 mutation is shown to interfere with CFTR interaction.

In those embodiments where protein:protein interaction is indicated by transcription of a detectable reporter gene, then any suitable DNA-binding domain and transcriptional activation domain can be used in the subject invention as long as the domains can be used to activate transcription of the detectable gene when the DNA-binding domain and transcriptional activation domain are brought into sufficiently close proximity to each other. The DNA-binding domain and transcriptional activation domain can be derived from the same protein or from different proteins. Examples of suitable domains are known in the art and can be obtained from, for example, yeast GAL4, GCN1 and ADR. In an exemplified embodiment of the invention, the domains are derived from yeast GAL4 protein. Non-yeast DNA-binding and/or transcriptional activation domains are also contemplated for use in the present invention and include, for example, a DNA-binding domain derived from the prokaryotic LexA protein and an 88-residue peptide (B42) capable of activating transcription (CLONTECH Laboratories, Palo Alto, Calif.). DNA-binding domains and transcriptional activation domains for use in mammalian host cells are also available.

The host cells can be any suitable prokaryotic or eukaryotic cell, including bacterial, yeast or mammalian cells. Preferably, the host cell is a yeast cell. More preferably, the yeast cell is *Saccharomyces*.

The interaction of the first hybrid protein and the second hybrid protein in the host cell causes a measurably greater expression of the detectable gene than that observed where the first hybrid protein and the second hybrid protein do not interact or interact at a reduced level. The detectable gene used in the present invention can be any gene whose transcription can be detected when the detectable gene is expressed as a result of the interaction of the CFTR fusion protein containing the DNA-binding and transcriptional activation domains. Typically, expression of the gene is detected directly or indirectly by detecting the expression product of the detectable gene. For example, the detectable gene may provide for drug resistance or encode an enzyme or other product that can be readily measured or detected. Such measurable activity may include providing the host cell with the ability to grow only when the detectable reporter gene is expressed, or providing for the presence of detectable protein or enzyme activity only when the detectable reporter gene is expressed. Suitable detectable genes are well known in the art. Examples of detectable genes include lacZ (which encodes β-galactosidase), HIS3, LEU2 and the like. In an exemplified embodiment, the detectable gene is the HIS3 gene. Host cells can be selected that lack or are defective in the detectable gene activity. Thus, if host cells that are normally unable to synthesize histidine are grown on a medium lacking histidine, then only those cells that are expressing the HIS3 gene as a result of CFTR protein interaction can grow, or at least grow at an efficient rate, on the medium lacking histidine. Growth of cells only in the presence of a test drug or compound is indicative that the drug or compound has restored interaction of the CFTR proteins. Methods for detecting protein interactions mediated by small molecule small ligands have been described in the art (Berlin, 1997).

In an exemplified embodiment of the invention, the NBD1 region of CFTR (containing amino acids 351-650) was cloned into two plasmids, pBDGAL4 and pADGAL4, (Stratagene) that produce the NBD1-DNA binding domain fusion protein and the NBD1-activation domain fusion protein, respectively, when co-expressed in yeast. When these proteins associate and form a dimer in yeast, transcription of the detectable gene occurs. The dimerization of the fusion proteins is required for growth of host cells in selective media. If the NBD1 coding region of one or both of the two plasmids is modified to contain the ΔF508 mutation and then expressed in yeast, the growth of the yeast is substantially impaired upon the selective media. The impaired growth of the yeast cells on the selective media results from the mutation(s) which prevent the dimerization of the proteins.

The subject invention also concerns unique host cells that can be used to model wildtype CFTR protein dimerization, and which can also be used to model the effect of CF mutations on dimerization. In a preferred embodiment, the host cells are yeast cells, such as *Saccharomyces cervisiae* or other suitable cells. The host cells are genetically engineered to express a hybrid protein that comprises a first human or other mammalian CFTR protein fused to a DNA binding domain of a transcriptional activator that can bind to a site on a detectable gene in the host cell. The host cells are also engineered to express a second hybrid protein that comprises human or mammalian CFTR protein fused to a transcriptional activator domain that can activate transcription of the detectable gene in the host cell when the transcriptional activator domain is brought into sufficiently close proximity with the detectable gene in the host cell. In a preferred embodiment, the portion of the CFTR protein expressed in the hybrid proteins is the first nucleotide binding domain (NBD1) of a human or other mammalian CFTR protein. In another embodiment, the first and/or second human or other mammalian CFTR protein that forms part of a hybrid protein in the host cell contains a mutation, such as, for example, the ΔF508 mutation. Using the host cells of the present invention, one can determine whether a particular mutation or mutations of one or both of the CFTR protein(s) will effect dimerization of the CFTR proteins. The host cells can be used in the methods of the present invention to detect interaction of CFTR proteins and to screen for drugs or compounds that can restore or enhance dimerization of CFTR proteins that contain mutations impacting dimerization.

The present invention also concerns methods and materials for screening and identifying compositions that restore or enhance interaction of CFTR proteins. In one embodiment, a method of the present invention for identifying a compound that facilitates interaction of CFTR polypeptides comprises contacting a host cell with the compound. Preferably, the host cell comprises a polynucleotide encoding a fusion protein comprising all or a portion of a first CFTR protein and a DNA binding domain of a transcriptional activator that can bind to a site on a detectable gene, and a polynucleotide encoding a fusion protein comprising all or a portion of a second CFTR polypeptide and a transcriptional activation domain of a transcriptional activator that can activate transcription of the detectable gene; however, the first or second CFTR polypeptides, or both the first and second polypeptides, used in the subject method comprise a mutation that reduces or prevents interaction of said fusion proteins. The polynucleotide encoding the first CFTR polypeptide and the second CFTR polypeptide are expressed in the host cell under conditions in which the detectable gene is expressed when the first CFTR polypeptide and the second CFTR polypeptide interact. If, in the presence of the test compounds, the detectable gene is expressed in the host cell at a level greater than the level of expression observed in the host cell in the absence of the compound, then that compound can be used in restoring interaction and dimerization of mutant CFTR polypeptides.

If either the first or second CFTR polypeptides, or both the first and second polypeptides used in the subject method comprise the temperature-sensitive ΔF508 mutation, interaction of the fusion proteins will be reduced when cells are incubated at the nonpermissive temperature. The polynucleotide encoding the first CFTR polypeptide and the second CFTR polypeptide are therefore expressed in the host cell incubated at the nonpermissive temperature resulting in impaired interaction between the first CFTR polypeptide and the second CFTR polypeptide, and reduced expression of the detectable gene. If a compound is added to the host cell incubated at the nonpermissive temperature, and the expression of the detectable gene is greater than the expression of the detectable gene in the host cell incubated at the nonpermissive temperature in the absence of the compound, then that compound can be used in restoring dimerization of CFTR polypeptides comprising the ΔF508 mutation.

The present invention concerns methods for screening chemical compounds for drug candidates with activity to correct the dimerization defect associated with mutant CFTR NBD1 containing the ΔF508 mutation. In the preferred embodiment, the YRG2-ΔF strain is spread at low density ($5.0 \times 10^6$ cells per plate) on the surface of selective yeast media in a petri dish plate. The media is SC-LEU-TRP-HIS (yeast nitrogen base w/o amino acids, and supplemented with all amino acids except leucine, tryptophan and histidine). Onto the surface of the plate is then placed one or more filter paper discs soaked in a solvent solution containing a test compound. The compound can be any small molecule of synthetic or natural product origin, or a natural product extract, and the solvent can be any suitable solvent with the preferred solvent being DMSO. The plate is incubated for one to three days at 37° C. A compound that demonstrates activity to correct the NBD1ΔF508 dimerization defect will diffuse into the media and cause the YRG2-ΔF yeast strain to grow at an increased rate in the proximity of the filter paper disc containing the active compound. The enhanced growth of the YRG2-ΔF yeast around a filter paper disc thus indicates the presence of an active compound within the test disc. If the sample tested is a pure compound, the compound can then be analyzed further in secondary assays to determine its activity to restore CFTRΔF508 cAMP-stimulated chloride channel activity in mammalian cells expressing CFTRΔF508 (Sheppard et al., 1994). If the sample being tested is a complex mixture of chemical compounds in a natural product extract, the extract can be fractionated by standard techniques and the fractions assayed using the YRG2-ΔF yeast as described above to identify fractions with the purified active compound. In another embodiment of the method, media used in screening compounds can contain 3-amino-2,3,4-triazole at a concentration of about 1.5 mM to make the assay more selective for compounds with high activity. In yet another embodiment of the method, the screening of compounds can be done using YRG2-ΔF grown in SC-LEU-TRP-HIS broth in microtiter plates incubated at 37° C. with test compounds added to the liquid culture. Compounds that correct the dimerization defect of YRG2-ΔF in this format will be detectable by detection of enhanced turbidity of individual micotiter wells containing an active compound.

The present invention also concerns plants and isolated extracts thereof that contain compounds or compositions that facilitate, enhance or restore dimerization of CFTR polypeptides. Plants that have tested positive for compounds capable of facilitating dimerization of CFTR polypeptides include *Trichilia* species. The present invention also concerns the compounds identified as facilitating, enhancing or restoring CFTR dimerization. Active compounds identified using the yeast mating and two-hybrid assays described herein can be purified from plants using standard biochemical function methods known in the art.

The present invention also concerns methods for screening plants for compounds of interest. In one embodiment, fragments of plant leaves are prepared from a plant to be tested and screened for bioactive compounds using a yeast-based assay of the present invention. A plant containing a compound that facilitates or enhances dimerization of mutant CFTR polypeptides is indicated by growth of yeast on a selective media. The methods described herein for screening the plants are efficient because a large number of plants can be tested on one petri dish and the results can be determined within a few days.

As exemplified herein, plants can be screened for bioactive compounds using a yeast two-hybrid assay according to the present invention. In the two hybrid methods of the invention, plants are screened using a yeast strain which contains a CF mutation that prohibits or interferes with the dimerization of CFTR proteins. In the absence of dimerization, the strain cannot grow on a selective media, such as, for example, a histidine-deficient media when the host cells are unable to synthesize histidine. Thus, growth of the yeast around plant tissue will be observed when the tissue contains a compound that enhances dimerization between the CFTR polypeptides in the yeast strain.

A composition that restores the ability of the hybrid proteins containing mutations in the CFTR proteins to interact can then be secondarily tested for activity to restore cAMP-stimulated chloride channel function in mammalian cells expressing CFTR having the same mutation. Drugs and compounds that restore dimerization and function in vitro can be further evaluated to confirm in vivo efficacy in treating clinical CF disease. Thus, the subject invention also concerns materials and methods for identifying compounds useful in treating CF.

The subject invention also concerns methods for treating CF by providing a drug or other compound that restores, promotes or enhances the dimerization of CFTR protein and/or its exit from ER. In one embodiment, an effective amount of a drug or compound identified using the methods of the present invention is administered to a CF patient. The amount of the drug or compound to be administered can be readily determined by the ordinarily skilled clinician having the benefit of the subject disclosure. If the drug or compound is a protein, then the drug or compound can also be provided to a CF patient by gene therapy methods. A polynucleotide sequence encoding the protein can be delivered to CF cells of a patient either in vivo or ex vivo using standard gene transfer methods and constructs. The drug or compound is expressed in the CF cell and thereby promotes dimerization of the mutant CFTR protein to enable the CFTR protein to properly localize and function as in a normal, non-CF cell.

The subject invention also concerns drugs, compounds, polypeptides and biologically active fragments thereof, antibodies or antigen binding fragments thereof, polynucleotides and other agents identified using the methods of the invention that restore, promote or enhance the in vivo dimerization of CFTR protein and/or its exit from ER in a cell. The drugs and compounds of the present invention can be used to treat CF patients according to the methods described herein.

The subject invention also concerns methods for screening for second site mutations that correct the defect in mutant CFTR. For example, using the methods of the subject invention, one can screen for mutations that correct a CFTR gene carrying the ΔF508 mutation. In one embodiment, the present invention can be used to screen for second site mutations that provide increased expression and function of CFTR that is greater than that observed for normal wildtype CFTR expression. The present invention also concerns mutant CFTR genes that contain second site mutations that correct the CF defect and provide increased expression and function of CFTR substantially the same as or greater than normal human wildtype CFTR.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods

Construction of plasmids and transformed yeast cells. The HYBRIZAP Two-Hybrid System (Stratagene, LaJolla, Calif.) was used for construction of gene fusions of the GAL4 activation domain and GAL4 DNA binding domain to CFTR NBD1. Fusion genes constructed with plasmids pAD-GAL4 and pBD-GAL4 were expressed in yeast strain YRG2 (genotype; Mat α, ura3-52, his3-200, ade2-101, lys2-801, trp1-901, leu2-3, 112, gal4-542, gal80-538, LYS2::UAS$_{GAL1}$-TATA$_{GAL1}$-HIS3 URA::UAS$_{GAL4\ 17mers(x3)}$ TATA$_{CYC1}$-lacZ). The plasmids pSWICK-CFTR (obtained from Dr. Michael Welsh, University of Iowa) and pSwick-CFTRΔF508 contain the full length wildtype CFTR cDNA and mutant CFTR cDNA (containing ΔF508) respectively. Derivatives of these plasmids (pSwick-BXWT and pSwick BXΔF respectively) that contain a Sma I restriction site at CFTR nucleotide position 1626 and a Xho I site at nucleotide position 1808 were constructed by site-directed mutagenesis.

First, a DNA fragment containing CFTR amino acids T351-S492 was produced using pSwick-BXWT plasmid DNA as template and the primers PRNBD1-R1 (5'-CGCG-GAATTCACTCGGCAATTTCCC-3') (SEQ ID NO:1) and PRNBD1-PST (5'-GCGCCTGCAGTTAAGAACAGAAT-GAAAT-3') (SEQ ID NO:2) in the polymerase chain reaction (PCR). The resulting 449 bp DNA fragment contained an Eco R1 restriction endonuclease site preceding the CFTR amino acid T351 and a Pst I site following CFTR amino acid S492. The fragment was restricted with EcoR1 and Pst I restriction endonucleases, and ligated into the unique Eco RI and Pst I restriction sites within pAD-GAL4 to produce pADPRNBD1 in which CFTR amino acids T351-S492 are joined in frame to the pAD-GAL4 transcription activation domain. A second GAL4-CFTR fusion plasmid was constructed in which a 951 bp HpaI-TaqI DNA fragment from pSwick-BXWT (containing CFTR amino acids R334-F650, and with the ends of the fragment made blunt by klenow fragment) was purified from an agarose gel and ligated into the Sma I site of plasmid pBDGAL4 to produce PBD-N. The pBD-N plasmid DNA was then cut with Eco RI and Bam HI and the vector molecule purified from an agarose gel. The purified Eco RI-Bam HI pBD-N vector molecule was then ligated to an Eco RI-Bam HI restriction fragment from pADPRNBD1 (containing amino acids T351-S492 of CFTR), producing pBDPN-WT. The pBDPN-WT plasmid contains CFTR amino acids T351-F650 fused in frame to the GAL4 DNA binding domain. This region contains the predicted cytosolic region that precedes NBD1, the NBD1 region, and also a segment that had previously been ascribed to the R domain. The plasmid pBDPN-WT also contains the TRP1 gene of yeast, and replication origin from the yeast 2μ plasmid. The Eco RI-Pst I fragment from pBDPN-WT (containing CFTR amino acids T351-F650) was then cloned into the EcoRI and Pst sites of pAD-GAL4, producing pADPN-WT. pADPN-WT contains CFTR amino acids T351-F650 fused in frame to the GAL4 activation domain. The pADPN-WT plasmid also contains the LEU2 gene of yeast and the replication origin of the yeast 21 circle. Both plasmids pBDPN-WT and pADPN-WT were introduced by transformation into yeast cell strain YGR-2 to produce cells designated as YRG2-WT.

A plasmid identical to pBDPN-WT, but containing the ΔF508 mutation (pBDPNAF) was constructed by cutting pBDPN-WT with Sma I and Xho I, and replacing the approximately 180 bp Sma I-Xho I fragment (containing the wildtype CFTR region P499-R560) with the corresponding Sma I-Xho I fragment from pSwick-BXAF containing the ΔF508 mutation. Similarly, a plasmid identical to pADPN-WT, but containing the ΔF508 mutation was constructed. Both plasmids pBDPN-ΔF and pADPN-ΔF were introduced by transformation into yeast cell strain YGR-2 to produce cells designated as YRG2-ΔF.

Example 1

Interaction of CFTR Proteins

A protein:protein interaction between the CFTR NBD1 polypeptide segment in each GAL4 fusion protein encoded by pBDPN-WT and pADPN-WT plasmids in YRG2-WT is expected to activate transcription of the HIS3 reporter gene in yeast, resulting in a HIS+ phenotype. Accordingly, the YRG2-WT strain was streaked onto agar plates containing synthetic complete media lacking tryptophan, leucine, and histidine (SC-HIS, -LEU, -TRP) to determine the HIS phenotype. As shown in Table 1, the YRG2-WT strain was phenotypically HIS+ at all temperatures tested (21° C., 30° C., and 34° C.), indicating that the two NBD1 fusion proteins associated in vivo to activate GAL4 transcription. The YRG2 strain containing either the pBDPN-WT plasmid or the pADPN-WT plasmid alone was unable to grow on media lacking histidine. The wildtype CFTR NBD1 segment is thus able to self-associate and form dimers at 21° C., 30° C. and 34° C. When grown in liquid culture media (SC-HIS, -LEU, -TRP), at 21° C., 30° C., and 34° C., the YRG2-WT yeast strain had a generation time of approximately 300, 138 and 420 minutes, respectively.

When the YRG2-ΔF strain was streaked onto solid media (SC-HIS, -LEU, -TRP) and incubated at 21° C., colonies formed within three days (Table 2). The YRG2-ΔF colonies were approximately the same size as colonies produced by YRG2-WT grown under the same conditions. However, when YRG2-ΔF was streaked onto SC-HIS-LEU-TRP solid media and incubated at 30° C., only small colonies were apparent after three days (substantially smaller in size than YRG2-WT colonies grown under the same growth conditions). Colonies were not apparent (or were detectable only as extremely small micro-colonies) when YRG2-ΔF was streaked onto solid SC-HIS, -LEU, -TRP media and incubated at 34° C. The ΔF508 mutation thus conferred a temperature-sensitive HIS+ phenotype to the yeast strain containing pADPN-ΔF and pBDPN-ΔF. To further enhance the temperature-sensitive HIS– colony phenotype of the YRG2-ΔF strain relative to the YRG2-WT strain, it is advantageous to incorporate 3-amino-1,2,4-triazole at a concentration of 1.5 mM into the SC-HIS-LEU-TRP media. The addition of 1.5 mM 3-amino-1,2,4-triazole to the SC-HIS-LEU-TRP media prevents colony formation of the YRG2-ΔF strain when grown at 30° C. for three days, but does not inhibit colony formation of the YRG2-WT strain grown under the same conditions.

The temperature-sensitive growth HIS+ phenotype was also observed when YRG2-ΔF was grown in SC-HIS-LEU-TRP liquid culture media at 21° C., 30° C. and 34° C. (Table 2). When incubated at 21° C., the generation time of YRG2-ΔF was observed to be approximately 400 minutes, which is comparable to the generation time of YRG2-WT under the same growth conditions. However, when incubated at 30° C., the generation time of YRG2-ΔF was approximately 1380 minutes, which is substantially longer than the generation time of the YRG2-WT strain (138 minutes) at this temperature. The generation time of YRG2-ΔF incubated at 34° C. (>4320 minutes) was also increased substantially as compared to YRG2-WT (420 minutes). These results indicate that the ΔF508 mutation interferes with the dimerization of NBD1 in a temperature-sensitive manner. Further, the effect of the ΔF508 mutation on YRG2-ΔF growth rate is analogous to the temperature-sensitive effect of ΔF508 on the processing of CFTRΔF508, indicating the folding defect of CFTRΔF508 has been faithfully modeled with the YRG2-ΔF yeast strain.

TABLE 1

Yeast Strain YRG2-WT

|  | 21° C. | 30° C. | 34° C. |
| --- | --- | --- | --- |
| Colony formation on solid agar media after 3 days (SC-HIS, -LEU, -TRP) | + | + | + |
| Generation time (min.) when grown in liquid culture medial (SC-HIS, -LEU, -TRP) | 300 | 138 | 420 |

TABLE 2

Yeast Strain YRG2-ΔF

|  | 21° C. | 30° C. | 34° C. |
| --- | --- | --- | --- |
| Colony formation on solid agar media after 3 days (SC-HIS, -LEU, -TRP) | + | +/– | – |
| Generation time (min.) when grown in liquid culture medial (SC-HIS, -LEU, -TRP) | 441 | 1380 | >4320 |

Example 2

Screening of Plants for Compounds Using the Yeast Two-Hybrid Assay

The YRG-F yeast strain used for this assay expresses two hybrid genes consisting of the N-terminal nucleotide binding domain of CFTR which contains the cystic fibrosis causing mutation ΔF508 (NBD1 ΔF508), fused to the DNA binding domain of the GAL4 transcription activator (GAL4BD) in the first hybrid and to the GAL4 activation domain (GAL4AD) of the second hybrid.

The yeast strain is used as a bioassay tool for the detection of dimerization of the NBD1 ΔF508 domain of CFTR. In the mutant human CFTR chloride channel containing the ΔF508 mutation, defective dimerization of the channel is impaired in a temperature-sensitive manner. Similarly, the dimerization of NBD1 ΔF508 in the YRG2-ΔF strain (the binding of the GAL4BD-NBD1 ΔF508 fusion protein to the GAL4AD-NBD1 ΔF508 fusion protein) is temperature-sensitive. In the absence of NBD1 ΔF508 dimerization, the YRG2-ΔF strain cannot activate transcription of the HIS3 gene which prevents the strain from growing on selective media lacking histidine at temperatures higher that 21° C.

Because the YRG2-ΔF strain is not capable of growing in a medium lacking the amino acid histidine as a result of defective NBD1 ΔF508 dimerization, it can be used in a plate assay to screen for compounds, such as those present in plant leaves, that promote the association of the two NBD1 ΔF508. The association of NBD1 ΔF508 brings the Gal4 activation and DNA binding domain together, thereby activating HIS3 synthesis and permitting growth of the yeast in a medium lacking histidine.

To use the YRG2-ΔF strain for screening purposes, a lawn of the YRG2-ΔF strain is spread onto selective media. This media contains yeast nitrogen base and all amino acids except for histidine, leucine, and tryptophan. The media also contains 3-amino 1,2,4-triazole at a concentration of 1.5 mM. The addition of the 3-amino 1,2,4-triazole to the media inhibits the residual HIS3 enzyme activity present in the YRG2-ΔF strain, thereby producing a tighter his– phenotype of the YRG2-ΔF strain on media lacking histidine. The YRG2-ΔF strain was added to the selective media, along with leaf discs to be screened and the plates were incubated at 30° C. for several days. Increased growth of the YRG2-ΔF strain around a leaf disc indicates the presence of a compound in the disc that reversed the ΔF508 dimerization defect. FIG. 1 shows a plate containing a leaf disc (denoted by arrow) that was positive for the presence of compounds that permitted growth of the YRG2-ΔF strain in the two-hybrid assay.

Example 3

Analysis of NBD1 Protein:Protein Interactions by the Yeast Two-Hybrid System

Because the ΔF508 mutation occurs in the NBD1 domain of CFTR, the dimerization of CFTR proteins may involve NBD1 and, thus, the ΔF508 mutation may result in defective NBD1 dimerization. To test whether NBD1 is able to dimerize in vivo, the two-hybrid system of yeast was utilized. The yeast two-hybrid system is an effective tool for demonstrating the binding interaction of two protein domains. The system is based on the well-characterized interaction of the DNA-binding domain (BD) and transcription-activation domain (AD) of the GAL4 transcription factor of yeast. The association of these two domains within the GAL4 protein results in the specific initiation of transcription of a reporter gene in yeast, but when these domains are expressed in yeast as separate domains, neither is capable of transcriptional activation in the absence of specific interaction with the other. The two-hybrid system was used to devise a phenotypic assay for the binding of the CFTR NBD1 domain to itself.

The DNA sequence encoding wildtype CFTR NBD1 T351-F650 was cloned in frame into the carboxy-terminus of the GAL4 DNA-binding domain on a yeast plasmid pBD-GAL4 (Stratagene). This plasmid (pBDGAL4-WT), contains a fusion protein consisting of the GAL4 DNA binding domain fused to CFTR NBD1 expressed under the control of the yeast ADH1 promoter and also contains the yeast selectable marker TRP1 and the 2µ origin of replication. The same segment of CFTR NBD1 was also cloned in frame into the GAL 4 activation domain on pADGAL4 (with the yeast selectable marker LEU2 and 2µ origin). This plasmid (pADGAL4-WT) contains a fusion protein consisting of the GAL transcription-activation domain fused to NBD1 expressed under the regulation of the ADH1 promoter, and also contains the LEU2 gene of yeast and the 2µ origin of replication.

Figures 2A, 2B, 2C:
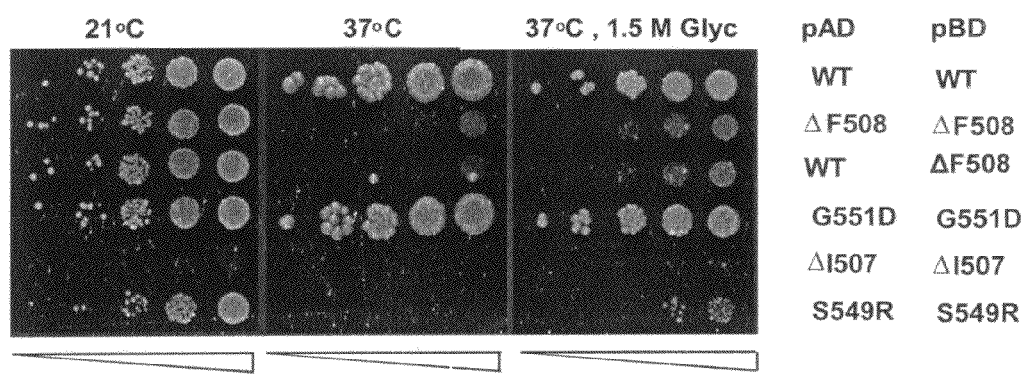
FIGS. 2A-2C show growth of two-hybrid yeast strains containing wildtype and mutant CFTR NBD1. The yeast strain YRG2 was transformed with pADGAL4 and pBD-GAL4 constructs containing wildtype and mutant CFTR NBD1 as indicated. Each strain was grown in synthetic complete media lacking leucine and tryptophan, and equal aliquots of cells in 10-fold dilutions were spotted to synthetic complete media lacking leucine, tryptophan and histidine. Dilutions for each strain proceed from right to left, with the spots from most dilute cultures corresponding to the tapered end of the triangle. Plates were incubated at either 21° C.

The two plasmids were transformed into yeast strain YRG2 to produce YRG2-WT. The YRG2 strain has the endogenous GAL4 transcription factor deleted and has auxotrophies trp1, leu2, and his3. Association of the two fusion proteins mediated by the interaction of NBD1 domains on each protein results in the transcriptional activation of the reporter gene, HIS3 that is regulated by GAL4 in YRG2. Activation of the HIS3 gene in yeast allows the YRG strain to grow on media lacking histidine, conferring a HIS+ phenotype. As shown in FIGS. 2A-2C, interaction between the NBD1 fusions in YRG-WT results in a HIS+ phenotype at both 21° C. and 37° C. The wildtype CFTR NBD1 segment is thus able to self-associate and form dimers.

The ΔF508 mutation was introduced into both pBDGAL4-WT and pADGAL4-WT, creating pBDGAL4-ΔF and pADGAL4-ΔF, respectively, and both plasmids were used to transform YRG2 (producing YRG-ΔF). Unlike the YRG-WT strain, the YRG-ΔF strain was phenotypically HIS– when tested for growth on selective media lacking histidine at 37° C. However, when tested for growth on selective media lacking histidine at 21° C. the YRG2 strain was phenotypically HIS+. Thus, the ΔF508 mutation conferred a temperature-sensitive HIS+ phenotype to the yeast strain containing pADΔF and pBDΔF, analogous to the temperature-sensitive processing defect observed for CFTRΔF508. A strain containing pBDΔF and pADWT (YRG-ΔF/WT) was also temperature-sensitive, indicating that heterodimers between a mutant ΔF508 NBD1 and a wildtype NBD1 could form at the permissive temperature (21° C.), but not at the nonpermissive temperature (37° C.). These results indicate that the ΔF508 mutation prevents the dimerization of NBD1 in a temperature-sensitive manner. Further, temperature-sensitive dimerization of mutant NBD1 containing the ΔF508 mutation is rescued by a concentration of 1.5M glycerol in the growth media (FIG. 2C), indicating that the same interventions that correct the CFTRΔF508 folding defect in animal cell cultures (Sato, 1996; Brown, 1996) also restored dimerization of the NBD1 in the yeast two-hybrid system.

To further assess the effect of CF mutations on dimerization of NBD1, CF-causing mutations were introduced into the pBD-WT and pAD-WT constructs and expressed these constructs in YRG2. As shown in FIGS. 2A-2C, the CF-causing mutations ΔI507 and S549R result in defective NBD1 dimerization. Like ΔF508, these mutations result in defective processing of CFTR. Another CF-causing mutations, G551D was also introduced into NBD1 within pBD-WT and pAD-WT, and did not result in defective NBD1 dimerization in yeast. In CFTR, the G551D mutation does not result in defective processing, but instead affects CFTR function. Defective dimerization of NBD1 was thus associated only with CF mutations that cause defective processing. These results suggest that the molecular defects associated with CF mutations are effectively modeled in yeast strain YRG2-ΔF.

The present invention is based upon the discovery that dimerization of NBD1 between CFTR protein monomers is required for processing of the CFTR, and that processing of CFTRΔF508 is defective because of an inability of mutant CFTR protein to form dimers. It follows that interventions that restore dimerization of mutant CFTR NBD1 containing the ΔF508 mutation, should also restore processing of CFTRΔF508. A small molecule drug or other compound that promotes dimerization of NBD1 would thus constitute a drug intervention that restores CFTRΔF508 processing and function.

Example 4

Preparation of Revertant Mutants that Restore Dimerization in ΔF508

Figure 3:
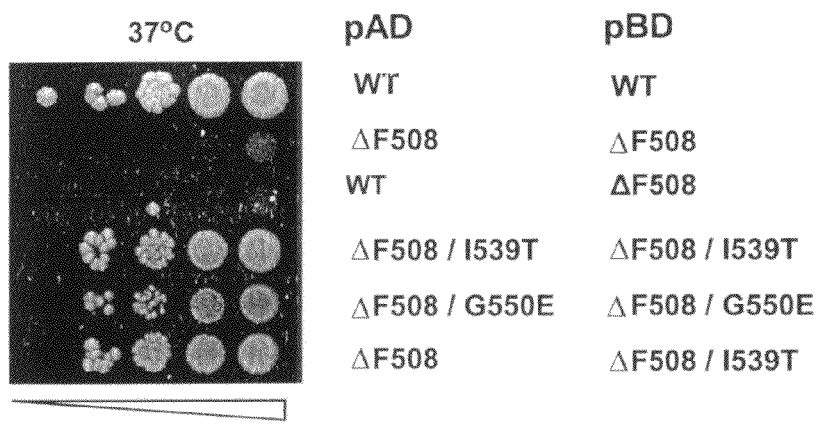
FIG. 3 shows correction of the ΔF508 dimerization defect by I539T and G550E. The yeast strain YRG2 (Stratagene) was transformed with pADGAL4 and pBDGAL4 constructs containing wildtype and mutant CFTR NBD1 as indicated. Each strain was grown in synthetic complete media lacking leucine and tryptophan, and equal aliquots of cells in 10-fold dilutions were spotted to synthetic complete media lacking leucine, tryptophan and histidine. Dilutions for each strain proceed from right to left, with the spots from most dilute cultures corresponding to the tapered end of the triangle. Plates were incubated at 37° C. for 5 days.

Second-site revertant mutations in NBD1 that restore dimerization of NBD1 would constitute a genetic intervention that restores CFTRΔF508 processing and function. Revertants of the ΔF508 dimerization defect were identified using the two-hybrid system. Revertant mutations would be expected to restore defective dimerization in yeast, and also correct the processing defect of CFTRΔF508 when introduced into a CFTRΔF508 cDNA allele expressed in mammalian cells. In order to isolate revertants of the ΔF508 dimerization defect, the fact that the formation of dimers between a wildtype NBD1 and mutant NBD1ΔF508 is defective at the nonpermissive temperature (FIGS. 2A-2C), as it is in YRG2-ΔF (where both NBD1 fusion proteins contain ΔF508) was exploited. If grown at the permissive temperature however, this "heterozygote" strain is HIS+ indicating that the mutant NBD1 is able to assume a wildtype-like conformation and form dimers with the wildtype NBD1 domain if allowed to fold at low temperature. Revertants of the ΔF508 dimerization defect can therefore be selected as mutations that occur in the mutant NBD1 and cause it to assume a configuration that is more like wildtype CFTR NBD1 at the nonpermissive temperature. The strategy for isolation of a ΔF508 dimerization revertant therefore involved in vitro mutagenesis of pBD-ΔF plasmid DNA, and subsequent transformation of this mutagenized DNA into YRG2 yeast containing the pAD-WT plasmid. It was anticipated that second-site mutations within the mutant NBD1 containing ΔF508 could restore heterodimer formation with wildtype NBD1, giving rise to transformants that were HIS+ at 37° C. Two revertant mutations of the ΔF508 dimerization defect, G550E and I539T, were identified as revertants of the ΔF508 dimerization defect in the two-hybrid system. I539T and G550E were introduced into plasmids pBD-ΔF and pAD-ΔF, transformed YRG2 and assayed the HIS phenotype of resulting transformants. As indicated in FIG. 3, the HIS+ phenotype of these strains (containing pBD-ΔF/I539T and pAD-ΔF/I539T or containing pBD-ΔF/G550E and pAD-ΔF/G550E) indicates that the I539T and G550E mutations restore in vivo dimerization of mutant NBD1 containing ΔF508.

Figure 4:
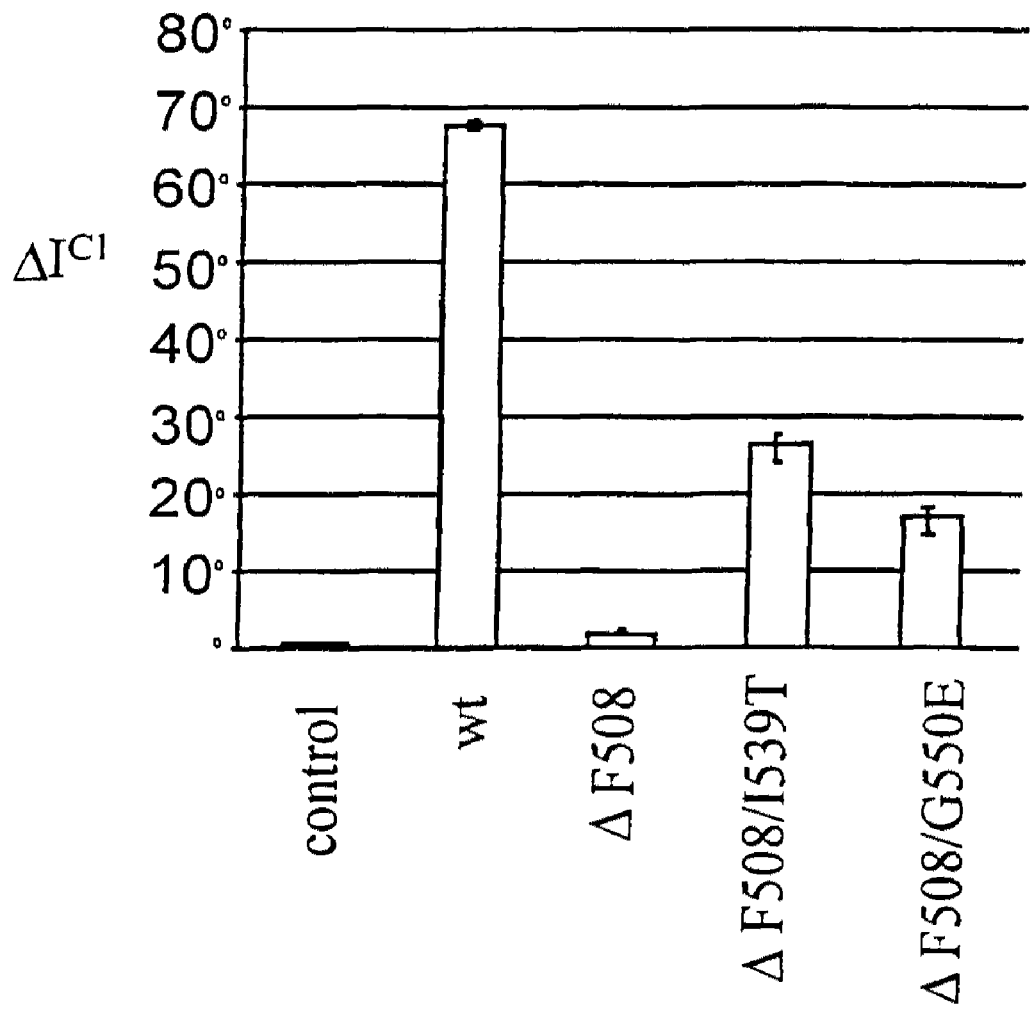
FIG. 4 shows the effect of the revertant mutations I539T and G550E on CFTRΔF508 chloride channel activity in FRT stable cell lines. FRT stable cell lines were seeded in permeable Millicell supports (Millipore) at a density of $2.5 \times 10^5$ cells/cm². After 6 to 7 days monolayers were mounted on Ussing chambers and the $\Delta I^{Cl}$ was recorded 5 min after stimulation with 10 mM forskolin and 0.1 mM IBMX (Sheppard et al., 1994).

To demonstrate that ΔF508 revertant mutations I539T and G550E restore processing of CFTRΔF508 in mammalian cells, CFTRΔF508 cDNA alleles containing either I539T or G550E were constructed for expression in mammalian cells. The I539T and G550E mutations were introduced into the plasmid expression vector pSWICK (Swick et al., 1992) (producing pSWICK-CFTRΔF508/I539T and pSWICK-CFTRΔF508/G550E) using oligonucleotide mutagenesis and the polymerase chain reaction. The pSWICK-CFTRΔF508/I539T plasmid DNA (15 μg.) and pSWICK-CFTRΔF508/G550E DNA (15 μg.) were then each mixed with 15 μg. of pcDNA3.1 plasmid DNA (Invitrogen), which contains the gene encoding Zeocin (Invitrogen) resistance. Each mixture of plasmid DNAs was then complexed with DMRIE-C lipid (Gibco) and used to transfect Fisher Rat Thyroid cells to obtain stable cell line transformants. Transformants were selected as Zeocin resistant colonies, that were then expanded and subcloned. Cell lines expressing either CFTRΔF508/I539T, CFTRΔF508/G550E, wildtype CFTR or mutant CFTRΔF508 were then grown as monolayers in Minicells, and mounted into Ussing chambers to assay for cAMP-stimulated chloride channel activity (Sheppard et al., 1994). As shown in FIG. 4, a control cell line expressing wildtype CFTR produces a cAMP-stimulated chloride current of approximately 67 μAmps/cm$^2$, whereas a cell line expressing CFTRΔF508 produces approximately 1.7 μAmps/cm$^2$. The cell lines expressing CFTRΔF508/I539T and CFTRΔF508/G550E each produced a significantly higher level of cAMP-stimulated chloride current (approximately 26 μAmps/cm$^2$ and 17 μAmps/cm$^2$, respectively) as compared to a cell line expressing CFTRΔF508, indicating that both revertant mutations restore CFTRΔF508 processing leading to functional CFTRΔF508 protein at the plasma membrane. These results indicate that a genetic intervention to correct dimerization of a mutant NBD1 results in correction of the CFTRΔF508 processing defect and increased CFTRΔF508 cAMP-stimulated chloride channel activity.

Example 5

Screening for Molecules to Correct the CFTRΔF508 Dimerization Defect

As a means for identifying small molecule candidate drugs that correct the CFTRΔF508 dimerization defect, the methods of the present invention were used to screen plants for compounds with activity to increase CFTRΔF508 chloride channel processing and function. The YRG2-ΔF strain was used to identify a plant of the genus *Trichilia* that produces a compound with activity to reverse the dimerization defect in YRG2-ΔF. An extract was prepared from leaf material of the plant and fractionated by standard methods. Fractions were assayed using the YRG2-ΔF strain to detect activity (i.e., activity to reverse the NBD1 dimerization defect resulting from the ΔF508 mutation). A compound with activity was purified from the plant extract and designated TS3. The TS3 compound was then assayed for activity to correct the CFTRΔF508 chloride channel defect in mammalian cells.

The TS3 compound was added at a concentration of 40 μM to the cell culture media of FRT cells grown in Millicells for three days. Cells were incubated in the presence of TS3 for an additional 72 hours. To assay cells for CFTRΔF508 cAMP-stimulated activity, the monolayers were mounted into Ussing chambers, cAMP agonists were added and the resulting peak change in chloride conductance was measured (Sheppard et al., 1994). Table 3 shows the mean cAMP-stimulated currents for untreated CFTRΔF508 expressing cells (n=4), and for CFTRΔF508 cells treated with TS3 for 48 hours (n=4). The results show that incubation of cells expressing the mutant CFTRΔF508 chloride channel with TS3 results in an approximately 70% increase in cAMP-stimulated chloride channel activity as compared to untreated cells expressing CFTRΔF508. This data indicates that the TS3 compound has activity to correct the molecular defect of CFTRΔF508 leading to increased functional activity at the plasma membrane. The data additionally demonstrate that the YRG2-ΔF yeast strain is an effective means to identify and purify compounds that have activity to correct the molecular defect causing cystic fibrosis.

TABLE 3

Effect of compound TS3 on cAMP-stimulated Cl− current from FRT cells expressing CFTRΔF508.

| | $\Delta I_{CL^-}/cm^2$ |
|---|---|
| TS3 (40 μm) | 2.06 ± 0.13 (n = 4) |
| No TS3 | 1.2 ± 0.11 (n = 4) |

Significance was calculated using the student's t-test (p < 0.001).

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Pat. No. 5,283,173
U.S. Pat. No. 5,468,614
U.S. Pat. No. 5,543,399
Aronheim A., E. Zandi, H. Hennemann, S. J. Elledge, M. Karin (1997) "Isolation of an AP-1 repressor by a novel method for detecting protein-protein interactions" *Mol Cell Biol* 17(6):3094-3102.
Berlin, V. (1997) "Protein interactions mediated by small molecule small ligands" *The Yeast Two-Hybrid System*, edited by Paul L. Bartel & Stanley Fields, Oxford University Press, New York.
Brown, C. R., L. Q. Hong-Brown, J. Biwersi, A. S. Verkman, W. J. Welch (1996) "Chemical chaperones correct the mutant phenotype of the delta F508 cystic fibrosis transmembrane conductance regulator protein" *Cell Stress Chaperones* 1:117-125.
Cheng, S. H., R. J. Gregory, J. Marshall, S. Paul, D. W. Souza, G. A. White, C. R. O'Riordan, A. E. Smith (1990) "Defective intracellular transport and processing of CFTR is the molecular basis of most cystic fibrosis" *Cell* 63:827-834.
Denning, G. M., M. P. Anderson, J. Amara, J. Marshall, A. E. Smith, M. J. Welsh (1992) "Processing of mutant CFTR (ΔF508) is temperature sensitive" *Nature* 358:761-764.
Flotte, T. R., S. A. Afione, P. L. Zeitlin (1994) "Adeno-associated virus vector gene expression occurs in nondividing cells in the absence of vector DNA integration" *Am J Respir Cell Mol Biol* 11:517-521.
Gregory, R. J., D. P. Rich, S. H. Cheng, D. W. Souza, S. Paul, P. Manavalan, M. P. Anderson, M. J. Welsh, A. E. Smith (1991) "Maturation and function of cystic fibrosis transmembrane conductance regulator variants bearing mutations in putative nucleotide-binding domains 1 and 2" *Mol Cell Biol* 11:3886-3893.
Johnsson and Varshavsky (1997) "Split ubiquitin, a sensor of protein interactions in vitro" *The Yeast Two-Hybrid System*, edited by Paul L. Bartel & Stanley Fields, Oxford University Press, New York.
Karimova G., J. Pidoux, A. Ullmann, D. Ladant (1998) "A bacterial two-hybrid system based on a reconstituted signal transduction pathway" *Proc Natl Acad Sci USA* 95(10):5752-5756.
Keegan et al. (1986) "Separation of DNA binding from the transcription activating function of a eukaryotic regulatory protein" *Science* 231:699-704.
Kerem, B.-S., J. M. Rommens, J.-A. Buchanan, D. Markiewicz, T. K. Cox, A. Chakravarti, M. Buchwald, L.-C. Tsui (1989) "Identification of the Cystic Fibrosis Gene: Genetic Analysis" *Science* 245:1073-1080.
Ma and Ptashne (1987) "Deletion analysis of GAL4 defines two transcriptional activating segments" *Cell* 48:847-853.
Riordan, J. R., J. M. Rommens, B-S Kerem, N. Alon, R. Rozmahel, Z. Grzelczak, J. Zielenski, S. Lok, N. Plavsic, J-L Chou, M. L. Drumm, M. C. Iannuzzi, F. S. Collins, L.-C. Tsui (1989) "Identification of the Cystic Fibrosis Gene: Cloning and characterization of complementary DNA" *Science* 245:1066-1073.
Rommens, J. M., M. C. Iannuzzi, B-S Kerem, M. L. Drumm, G. Melmer, M. Dean, R. Rozmahel, J. L. Cole, D. Kennedy, N. Hidaka, M. Zsiga, M. Buchwald, J. R. Riordan, L.-C. Tsui, F. Collins (1989) "Identification of the Cystic Fibrosis gene: Chromosome walking and jumping" *Science* 245: 1059-1065.
Sato, S., C. L. Ward, M. E. Krouse, J. J. Wine, R. R. Kopito (1996) "Glycerol reverses the misfolding phenotype of the most common cystic fibrosis mutation" *J Biol Chem* 271: 635-638.
Sheppard, D. N., D. P. Rich, L. S. Ostedgaard, R. J. Gregory, A. E. Smith, M. J. Welsh. (1993) "Mutations in CFTR associated with mild-disease-form Cl-channels with altered pore properties" *Nature* 362:160-164.
Sheppard, D. N., M. R. Carson, L. S. Ostedgaard, G. M. Denning, M. J. Welsh (1994) "Expression of cystic fibrosis transmembrane conductance regulator in a model epithelium" *Am J Physiol* 266:L405-413.
Swick, A. G., M. Janicot, T. Cheneval-Kastelic, J. C. McLenithan, M. D. Lane (1992) "Promoter-cDNA-directed heterologous protein expression in *Xenopus laevis* oocytes" *Proc Natl Acad Sci USA* 89:1812-1816.
Teem, J. L., H. A. Berger, L. O. Ostedgaard, D. P. Rich, L-C Tsui, M. J. Welsh (1993) "Identification of revertants for the cystic fibrosis ΔF508 mutation using STE6-CFTR chimeras in yeast" *Cell* 73:335-346.
Teem, J. L., M. Carson, M. J. Welsh (1996) "Mutation of R555 in CFTR-ΔF508 Enhances Function and Partially Corrects Defective Processing" *Receptors and Channels* 4:63-72.
Welsh, M. J., A. E. Smith, J. Zabner, D. P. Rich, S. M. Graham, R. J. Gregory, B. M. Pratt, R. A. Moscicki (1994) "Cystic fibrosis gene therapy using an adenovirus vector: in vivo safety and efficacy in nasal epithelium" *Hum Gene Ther* 5:209-219.
Welsh, M. J., A. E. Smith (1995) "Cystic fibrosis" *Sci Am* 273:52-59.
Zabner, J., L. A. Couture, R. J. Gregory, S. M. Graham, A. E. Smith, M. J. Welsh (1993) "Adenovirus-mediated gene transfer transiently corrects the chloride transport defect in nasal epithelia of patients with cystic fibrosis" *Cell* 75:207-216.
Zabner, J., S. H. Cheng, D. Meeker, J. Launspach, R. Balfour, M. A. Perricone, J. E. Morris, J. Marshall, A. Fasbender, A. E. Smith, M. J. Welsh (1997) "Comparison of DNA-lipid complexes and DNA alone for gene transfer to cystic fibrosis airway epithelia in vivo" *J Clin Invest* 100:1529-1537.

I claim:

1. A method of determining whether a compound restores or enhances interaction of CFTR polypeptides, said method comprising:

(a) contacting a host cell with said compound, wherein said host cell comprises a polynucleotide encoding a fusion protein comprising all or a portion of a first CFTR protein and a DNA binding domain of a transcriptional activator that can bind to a site on a detectable gene, wherein said first CFTR polypeptide comprises a first nucleotide binding domain (NBD1) of a CFTR polypeptide, or a functional fragment of said NBD1, and said host cell comprises a polynucleotide encoding a fusion protein comprising all or a portion of a second CFTR polypeptide and a transcriptional activation domain of a transcriptional activator that can activate transcription of a detectable gene, wherein said second CFTR polypeptide comprises an NBD1 of a CFTR polypeptide, or a functional fragment of said NBD1, and wherein said host cell further comprises said detectable gene wherein transcription of said detectable gene is under control of said transcriptional activator, wherein one or both of said first and second CFTR polypeptides comprise a mutation in said NBD1 that reduces or prevents interaction of said fusion proteins;

(b) expressing said polynucleotide encoding said first CFTR polypeptide and expressing said polynucleotide encoding said second CFTR polypeptide under conditions in which said detectable gene is expressed when said NBD1 of said first CFTR polypeptide and said NBD1 of said second CFTR polypeptide interact; and, (c) determining whether said detectable gene is expressed in said host cell at a level greater than the level of expression observed in said host cell in the absence of said compound.

2. The method according to claim 1, wherein said host cell is a yeast cell.

3. The method according to claim 2, wherein said yeast cell is *Saccharomyces*.

4. The method according to claim 1, wherein the host cell is a mammalian cell.

5. The method according to claim 1, wherein one or both of said first and second CFTR polypeptide is a mammalian CFTR polypeptide.

6. The method according to claim 1, wherein one or both of said first and second CFTR polypeptide comprises amino acid residue 351 through 650 of the human CFTR protein sequence.

7. The method according to claim 1, wherein said detectable gene is selected from the group consisting of lacZ, LEU2 and HIS3.

8. The method according to claim 1, wherein said DNA binding domain comprises the DNA binding domain of GAL4 protein.

9. The method according to claim 1, wherein said transcriptional activation domain comprises the transcriptional activation domain of GAL4 protein.

10. The method according to claim 1, wherein one or both of said first and second CFTR polypeptide contains a $\Delta$F508 mutation.

11. The method according to claim 1, wherein said compound is present in a plant and said host cell is contacted with a tissue sample from said plant.

12. The method according to claim 11, wherein said tissue sample is a leaf disc from said plant.

13. The method according to claim 1, wherein said host cell is contacted with said compound present or absorbed on a filter paper disc.

14. The method according to claim 1, wherein increased growth of said host cells is used for determining whether said detectable gene is expressed in said host cells at a level greater than the level of expression observed in said host cells in the absence of said compound.

15. The method according to claim 1, wherein said compound is selected from the group consisting of a polypeptide or a biologically active fragment thereof, an antibody or antigen binding fragment thereof, and a polynucleotide.

16. The method according to claim 1, wherein said compound is a compound from a library of compounds.

17. The method according to claim 1, wherein said compound is a synthetic compound.

18. The method according to claim 1, wherein said compound is a naturally occurring product.

19. The method according to claim 10, wherein said host cell is maintained at a nonpermissive temperature for said CFTR polypeptide containing said $\Delta$F508 mutation.

* * * * *

UNITED STATES PATENT AND TRADEMARK OFFICE
CERTIFICATE OF CORRECTION

PATENT NO. : 8,288,107 B2
APPLICATION NO. : 11/821812
DATED : October 16, 2012
INVENTOR(S) : John L. Teem Page 1 of 1

It is certified that error appears in the above-identified patent and that said Letters Patent is hereby corrected as shown below:

Column 3
Line 49, "$\Delta I^{Cl}$" should read -- $\Delta I^{Cl}$ --

Column 4
Line 42, "UASG" should read -- $UAS_G$ --

Column 10
Line 66, "yeast 21" should read -- yeast 2μ --

Column 11
Line 4, "(pBDPNAF)" should read -- (pBDPNΔF) --

Signed and Sealed this
Twelfth Day of February, 2013

Teresa Stanek Rea
*Acting Director of the United States Patent and Trademark Office*

SEQUENCE LISTING

```
<160> NUMBER OF SEQ ID NOS: 4

<210> SEQ ID NO 1
<211> LENGTH: 25
<212> TYPE: DNA
<213> ORGANISM: Homo sapien

<400> SEQUENCE: 1
cgcggaattc actcggcaat ttccc                                           25
```

<210> SEQ ID NO 2
<211> LENGTH: 28
<212> TYPE: DNA
<213> ORGANISM: Homo sapien

<400> SEQUENCE: 2
gcgcctgcag ttaagaacag aatgaaat                                           28

<210> SEQ ID NO 3
<211> LENGTH: 4443
<212> TYPE: DNA
<213> ORGANISM: Homo sapien
<220> FEATURE:
<221> NAME/KEY: gene
<222> LOCATION: (1)..(4443)

<400> SEQUENCE: 3

```
atgcagaggt cgcctctgga aaaggccagc gttgtctcca aacttttttt cagctggacc        60
agaccaattt tgaggaaagg atacagacag cgcctggaat tgtcagacat ataccaaatc       120
ccttctgttg attctgctga caatctatct gaaaaattgg aaagagaatg ggatagagag       180
ctggcttcaa agaaaaatcc taaactcatt aatgcccttc ggcgatgttt tttctggaga       240
tttatgttct atggaatctt tttatattta ggggaagtca ccaaagcagt acagcctctc       300
ttactgggaa gaatcatagc ttcctatgac ccggataaca aggaggaacg ctctatcgcg       360
atttatctag cataggctt atgccttctc tttattgtga ggacactgct cctacaccca       420
gccattttg gccttcatca cattggaatg cagatgagaa tagctatgtt tagtttgatt       480
tataagaaga ctttaaagct gtcaagccgt gttctagata aataagtat tggacaactt       540
gttagtctcc tttccaacaa cctgaacaaa tttgatgaag acttgcatt ggcacatttc       600
gtgtggatcg ctccttttgca agtggcactc ctcatggggc taatctggga gttgttacag       660
gcgtctgcct tctgtggact tggtttcctg atagtccttg ccctttttca ggctgggcta       720
gggagaatga tgatgaagta cagagatcag agagctggga agatcagtga aagacttgtg       780
attacctcag aaatgattga aaatatccaa tctgttaagg catactgctg ggaagaagca       840
atggaaaaaa tgattgaaaa cttaagacaa acagaactga aactgactcg gaaggcagcc       900
tatgtgagat acttcaatag ctcagccttc ttcttctcag ggttctttgt ggtgttttta       960
tctgtgcttc cctatgcact aatcaaagga atcatcctcc ggaaaatatt caccaccatc      1020
tcattctgca ttgttctgcg catggcggtc actcggcaat tccctgggc tgtacaaaca      1080
tggtatgact ctcttggagc aataaacaaa atacaggatt tcttacaaaa gcaagaatat      1140
aagacattgg aatataactt aacgactaca gaagtagtga tggagaatgt aacagccttc      1200
tgggaggagg gatttgggga attatttgag aaagcaaaac aaaacaataa aatagaaaaa      1260
acttctaatg gtgatgacag cctcttcttc agtaatttct cacttcttgg tactcctgtc      1320
ctgaaagata ttaatttcaa gatagaaaga ggacagttgt tggcggttgc tggatccact      1380
ggagcaggca agacttcact tctaatgatg attatgggag aactggagcc ttcagagggt      1440
aaaattaagc acagtggaag aatttcattc tgttctcagt ttcctggat tatgcctggc      1500
accattaaag aaaatatcat ctttggtgtt cctatgatg aatatagata cagaagcgtc      1560
atcaaagcat gccaactaga agaggacatc tccaagtttg cagagaaaga caatatagtt      1620
cttggagaag gtggaatcac actgagtgga ggtcaacgag caagaatttc tttagcaaga      1680
gcagtataca agatgctga tttgtatta ttagactctc cttttggata cctagatgtt      1740
```

```
ttaacagaaa aagaaatatt tgaaagctgt gtctgtaaac tgatggctaa caaaactagg    1800 atttggtca  cttctaaaat ggaacattta aagaaagctg acaaaatatt aattttgcat    1860
gaaggtagca gctattttta tgggacattt tcagaactcc aaaatctaca gccagacttt    1920
agctcaaaac tcatgggatg tgattctttc gaccaattta gtgcagaaag aagaaattca    1980
atcctaactg agaccttaca ccgtttctca ttagaaggag atgctcctgt ctcctggaca    2040
gaaacaaaaa aacaatcttt taaacagact ggagagtttg gggaaaaaag gaagaattct    2100
attctcaatc caatcaactc tatacgaaaa ttttccattg tgcaaaagac tcccttacaa    2160
atgaatggca tcgaagagga ttctgatgag cctttagaga aaggctgtc  cttagtacca    2220 gattctgagc agggagaggc gatactgcct cgcatcagcg tgatcagcac tggccccacg    2280
cttcaggcac gaaggaggca gtctgtcctg aacctgatga cacactcagt taaccaaggt    2340
cagaacattc accgaaagac aacagcatcc acacgaaaag tgtcactggc ccctcaggca    2400
aacttgactg aactggatat atattcaaga aggttatctc aagaaactgg cttgaaaata    2460
agtgaagaaa ttaacgaaga agacttaaag gagtgctttt ttgatgatat ggagagcata    2520
ccagcagtga ctacatggaa cacatacctt cgatatatta ctgtccacaa gagcttaatt    2580
tttgtgctaa tttggtgctt agtaattttt ctggcagagg tggctgcttc tttggttgtg    2640
ctgtggctcc ttggaaacac tcctcttcaa gacaaaggga atagtactca tagtagaaat    2700
aacagctatg cagtgattat caccagcacc agttcgtatt atgtgtttta catttacgtg    2760
ggagtagccg acactttgct tgctatggga ttcttcagag tctaccact  ggtgcatact    2820 ctaatcacag tgtcgaaaat tttacaccac aaaatgttac attctgttct tcaagcacct    2880
atgtcaaccc tcaacacgtt gaaagcaggt gggattctta atagattctc caaagatata    2940
gcaattttgg atgaccttct gcctcttacc atatttgact tcatccagtt gttattaatt    3000
gtgattggag ctatagcagt tgtcgcagtt ttacaaccct acatctttgt tgcaacagtg    3060
ccagtgatag tggcttttat tatgttgaga gcatatttcc tccaaacctc acagcaactc    3120
aaacaactgg aatctgaagg caggagtcca attttcactc atcttgttac aagcttaaaa    3180
ggactatgga cacttcgtgc cttcggacgg cagccttact ttgaaactct gttccacaaa    3240
gctctgaatt tacatactgc caactggttc ttgtacctgt caacactgcg ctggttccaa    3300
atgagaatag aaatgatttt tgtcatcttc ttcattgctg ttaccttcat ttccattta    3360 acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggcctcagg  gggccaaatg actgtcaaag atctcacagc aaaatacaca    3660
gaaggtggaa atgccatatt agaacatt  tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga aagcctttgg agtgatacca cagaaagtat ttatttttc  tggaacattt    3900 agaaaaaact tggatcccta tgaacagtgg agtgatcaag aaatatggaa agttgcagat    3960
gaggttgggc tcagatctgt gatagaacag tttcctggga agcttgactt tgtccttgtg    4020 gatggggct  gtgtcctaag ccatggccac aagcagttga tgtgcttggc tagatctgtt    4080
ctcagtaagg cgaagatctt gctgcttgat gaacccagtg ctcatttgga tccagtaaca    4140
```

-continued

```
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagcccagat ttgctgctct gaaagaggag acagaagaag aggtgcaaga tacaaggctt    4440
tag                                                                  4443
```

<210> SEQ ID NO 4
<211> LENGTH: 1480
<212> TYPE: PRT
<213> ORGANISM: Homo sapien
<220> FEATURE:
<221> NAME/KEY: PEPTIDE
<222> LOCATION: (1)..(1480)

<400> SEQUENCE: 4

```
Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
             20                  25                  30

Glu Leu Ser Asp Ile Tyr Gln Ile Pro Ser Val Asp Ser Ala Asp Asn
         35                  40                  45

Leu Ser Glu Lys Leu Glu Arg Glu Trp Asp Arg Glu Leu Ala Ser Lys
     50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300
```

-continued

```
Phe Asn Ser Ser Ala Phe Phe Ser Gly Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
                355                 360                 365

Asn Lys Ile Gln Asp Phe Leu Gln Lys Gln Glu Tyr Lys Thr Leu Glu
                370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
                435                 440                 445

Glu Arg Gly Gln Leu Leu Ala Val Ala Gly Ser Thr Gly Ala Gly Lys
450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
                515                 520                 525

Asp Ile Ser Lys Phe Ala Glu Lys Asp Asn Ile Val Leu Gly Glu Gly
                530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
                580                 585                 590

Lys Leu Met Ala Asn Lys Thr Arg Ile Leu Val Thr Ser Lys Met Glu
                595                 600                 605

His Leu Lys Lys Ala Asp Lys Ile Leu Ile Leu His Glu Gly Ser Ser
                610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
                660                 665                 670

Gly Asp Ala Pro Val Ser Trp Thr Glu Thr Lys Lys Gln Ser Phe Lys
                675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735
```

```
Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Gln Ser
            755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
        850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
        1075                1080                1085

Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
                1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
```

-continued

```
                1155                1160                1165
Met Pro Thr Glu Gly Lys Pro Thr Lys Ser Thr Lys Pro Tyr Lys Asn
    1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
                1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
        1235                1240                1245

Gly Lys Ser Thr Leu Leu Ser Ala Phe Leu Arg Leu Leu Asn Thr Glu
    1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
                1285                1290                1295

Ser Gly Thr Phe Arg Lys Asn Leu Asp Pro Tyr Glu Gln Trp Ser Asp
            1300                1305                1310

Gln Glu Ile Trp Lys Val Ala Asp Glu Val Gly Leu Arg Ser Val Ile
        1315                1320                1325

Glu Gln Phe Pro Gly Lys Leu Asp Phe Val Leu Val Asp Gly Gly Cys
    1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
                1365                1370                1375

Asp Pro Val Thr Tyr Gln Ile Ile Arg Arg Thr Leu Lys Gln Ala Phe
            1380                1385                1390

Ala Asp Cys Thr Val Ile Leu Cys Glu His Arg Ile Glu Ala Met Leu
        1395                1400                1405

Glu Cys Gln Gln Phe Leu Val Ile Glu Glu Asn Lys Val Arg Gln Tyr
    1410                1415                1420

Asp Ser Ile Gln Lys Leu Leu Asn Glu Arg Ser Leu Phe Arg Gln Ala
1425                1430                1435                1440

Ile Ser Pro Ser Asp Arg Val Lys Leu Phe Pro His Arg Asn Ser Ser
                1445                1450                1455

Lys Cys Lys Ser Lys Pro Gln Ile Ala Ala Leu Lys Glu Glu Thr Glu
            1460                1465                1470

Glu Glu Val Gln Asp Thr Arg Leu
        1475                1480
```